United States Patent
Mouton

(10) Patent No.: US 9,314,019 B2
(45) Date of Patent: *Apr. 19, 2016

(54) SNOUT BEETLE ATTRACTANT

(71) Applicant: Schalk Francois Mouton, Citrusdal (ZA)

(72) Inventor: Schalk Francois Mouton, Citrusdal (ZA)

( * ) Notice: Subject to any disclaimer, the term of this patent is extended or adjusted under 35 U.S.C. 154(b) by 31 days.

This patent is subject to a terminal disclaimer.

(21) Appl. No.: 13/961,346

(22) Filed: Aug. 7, 2013

(65) Prior Publication Data

US 2013/0315971 A1 Nov. 28, 2013

Related U.S. Application Data

(63) Continuation of application No. PCT/IB2012/050610, filed on Feb. 10, 2012.

(30) Foreign Application Priority Data

Feb. 10, 2011 (ZA) .................................. 2011/01084

(51) Int. Cl.
| | |
|---|---|
| *A01N 53/00* | (2006.01) |
| *A01N 35/02* | (2006.01) |
| *A01N 43/08* | (2006.01) |
| *A01N 31/14* | (2006.01) |
| *A01N 35/04* | (2006.01) |
| *A01N 37/08* | (2006.01) |

(52) U.S. Cl.
CPC ................ *A01N 37/08* (2013.01); *A01N 31/14* (2013.01); *A01N 35/02* (2013.01); *A01N 35/04* (2013.01); *A01N 43/08* (2013.01); *A01N 53/00* (2013.01)

(58) Field of Classification Search
CPC ....... A01N 43/08; A01N 37/08; A01N 31/14; A01N 35/02; A01N 35/04
See application file for complete search history.

(56) References Cited

U.S. PATENT DOCUMENTS 5,788,975 A   8/1998 Laversanne et al.
8,713,849 B2 *  5/2014 Mouton .......................... 43/108

FOREIGN PATENT DOCUMENTS

EP   0 319 757 A2   6/1989
JP   05-310504 A   11/1993

OTHER PUBLICATIONS

Mason, J.R. et al., "Effectiveness of thirteen vertebrate repellents as rodent trigeminal stimulants," Physiology & Behavior, vol. 6, No. 6, pp. 1449-1452 (1996).*
Sivakumar, P.M. et al., "Experimental and QSAR of acetophenone as antibacterial agents," Chemical Biology & Drug Design, vol. 72, pp. 303-313 (2008).*
Hacley, E.A.C., "Tests of Attractants for the Palm Weevil", Journal of Economic Entomology, vol. 58, No. 5, Oct. 1965, pp. 1002-1003.
Leal et al., "Aggregation of the Scarab Beetle Holotrichia consanguinea in response to Female-Released Pheromone Suggest Secondary Function Hypothesis for Semiochemical", Journal of Chemical Ecology, 1996, vol. 22, No. 8, pp. 1557-1566.
Rochat et al., "Identification of Pheromone Synergists in American Palm Weevil, *Rhynchophorus palmarum*, and Attraction of Related Dynamis borassi", Journal of Chemical Ecology, 2000. vol. 26, No. 1, pp. 155-187.
Ward et al., "Identification of the Sex Pheromone of Holotrichia reynaudi", Journal of Chemical Ecology, 2002, vol. 28, No. 3, pp. 515-522.
International Application No. PCT/IB2012/050610 International Search Report and Written Opinion, mailed May 30, 2012.
Kelts, C.A., Evaluation of Attractants and Monitoring of Sap Beetle Control in Strawberries, 2005, Masters Thesis, University of Florida.
Marques et al., "Response of Diabrotica speciosa (Coleoptera: Chrysomelidae) to 1, 4-Dimethoxybenzene and Analogs in common Bean Crop" Brazilian Archives of Biology and Technology, vol. 52, No. 6, pp. 1333-1340.
Yano, K. and Tanaka, N., "Antifeedant Activity toward Larvae of Pieris rapae crucivora of Aromatic Carbonyl Compounds Related to Capillin Isolated from Artemisia capillaris", Bioscience Biotechnology and Biochemistry, 1995, vol. 59, issue 6, pp. 1130-1132.

* cited by examiner

*Primary Examiner* — John Pak
(74) *Attorney, Agent, or Firm* — Woodard, Emhardt, Moriarty, McNett & Henry LLP

(57) ABSTRACT

An odorant substance for use in as an attractant for snout beetles and a method for controlling snout beetles are provided. The odorant substance includes at least one of: Cyclopropane carboxylic acid; 5-Methyl-2-hexanone; 2,5-Dimethyl-4-methoxy-3(2H)-furanone ("Mesifurane or berry furanone"); Anisole; and 3-Methoxy acetophenone. The method of controlling snout beetles includes applying the odorant substance to attract the snout beetles, e.g. by applying the substance to mechanical traps, combining the substances with insecticides, or the like.

13 Claims, No Drawings

SNOUT BEETLE ATTRACTANT

CROSS-REFERENCE TO RELATED APPLICATIONS

This application is a continuation of International Patent Application No. PCT/IB2012/050610 filed Feb. 10, 2012, which claims the benefit of South Africa Patent Application No. 2011/01084 filed Feb. 10, 2011, which are hereby referenced in their entireties.

FIELD OF THE INVENTION

This invention relates to the control and in particular, the attraction of snout beetles (true weevils), particularly *Eremnus setulosus* and *Phlyctinus colosus*.

BACKGROUND TO THE INVENTION

Snout beetles damage crops such as fruits and the present invention seeks to prevent or at least inhibit such damage.

Snout beetles are small insects that over-winter in the soil as pupae, which hatch in early spring and then crawl up the stems of plants such as vines or fruit trees to feed in the canopies on leafs and young fruits.

Snout beetle populations can be controlled by mass application of pesticides, e.g. by cover sprays of the trees.

The present invention seeks to provide an effective attractant (odorant compound or combination) for snout beetles, which can be used in effective and environmentally sound pest control to minimise cover sprays with their concomitant residue problems.

SUMMARY OF THE INVENTION

According to one aspect of the present invention there is provided an odorant substance for use in as an attractant for snout beetles, said odorant substance including at least one, or each of the following compounds:
 Cyclopropane carboxylic acid;
 5-Methyl-2-hexanone;
 2,5-Dimethyl-4-methoxy-3(2H)-furanone ("Mesifurane or berry furanone");
 Anisole; and
 3-Methoxy acetophenone.

The substance may include each of the compounds: Cyclopropane carboxylic acid, 5-Methyl-2-hexanone, 2,5-Dimethyl-4-methoxy-3(2H)-furanone, and Anisole and the compounds may be included in the substance in generally equal parts, by volume. The substance is contained in a capsule with a polymeric wall through which the compounds can pass by diffusion.

The substance may include 20% 3-Methoxy acetophenone, diluted in water, by volume.

According to another aspect of the present invention there is provided a method of controlling snout beetles, said method including the step of applying the odorant substance described herein above, to attract the snout beetles, e.g. by applying the odorant substance to mechanical traps, combining the odorant substances with insecticides, or the like.

The method may include placing a capsule containing at least one of Cyclopropane carboxylic acid, 5-Methyl-2-hexanone, 2,5-Dimethyl-4-methoxy-3(2H)-furanone, and Anisole in the mechanical trap, and the capsule may have a polymeric wall through which said compounds can pass by diffusion. The capsule may contain each of the Cyclopropane carboxylic acid, 5-Methyl-2-hexanone, 2,5-Dimethyl-4-methoxy-3(2H)-furanone, and Anisole in generally equal parts, by volume.

The method may include applying a 20% dilution of said 3-Methoxy acetophenone in water, by volume, to a surface of the mechanical trap.

The snout beetles may be *Eremnus setulosus* and/or *Phlyctinus calosus*.

EXPERIMENTS

For a better understanding of the present invention, and to show how the same may be carried into effect, the invention will now be described by way of non-limiting example, with reference to practical experiments, to assess the extent to which different test odorants attracted snout beetles.

Experimental Procedure for Individual Odorants

Yellow Delta traps fitted with bottom sticky pads upon which odorant dispensers of the various test odorants were applied, were placed on ground level against the trunks of bearing apple trees in the Koue Bokkeveld area in the Western Cape Province, South Africa. Test orchards infested with snout beetles were selected on the farms Dennekruin and Voorsorg in the Ceres-Koue-Bokkeveld area.

Unloaded or "blank" traps with no odorants, but identical to the other traps in all other respects, were used as a control. There are no attractants registered for use on snout beetles on deciduous fruit in South Africa with which to compare the experimental results.

After one week the traps were collected and the snout beetles caught were counted and noted. Six replications were used per odorant tested. In Table 1 below the summarised results of the experiments are presented.

Results

TABLE 1

Numbers of snout beetles caught in yellow Delta traps.

| Attractant/ odorant | Rep. 1 | Rep. 2 | Rep. 3 | Rep. 4 | Rep. 5 | Rep. 6 | Mean |
| --- | --- | --- | --- | --- | --- | --- | --- |
| Blank control | 0 | 0 | 0 | 0 | 0 | 0 | 0 |
| Cyclopropane carboxylic acid | 6 | 7 | 5 | 7 | 3 | 19 | 7.8 |
| 2,5-Dimethyl-4-methoxy-3(2H)-furanone | 2 | 4 | 3 | 2 | 3 | 7 | 3.5 |
| Anisole | 4 | 1 | 3 | 3 | 2 | 3 | 2.7 |
| 5-Methyl-2-hexanone | 4 | 1 | 1 | 5 | 3 | 2 | 2.7 |
| 3-Methoxy acetophenone | 3 | 1 | 6 | 2 | 1 | 2 | 2.5 |

Comments

The strongest attraction of snout beetles was achieved from Cyclopropane carboxylic acid with a mean trap catch of 7.8 snout beetles from six replications. By comparison, the mean of trap catches traps with 2,5-Dimethyl-4-methoxy-3(2H)-furanone was 3.5 and the mean of trap catches with each of anisole and 5-Methyl-2-hexanone, was 2.7. 3-Methoxy-acetophenone caught 2.5 snout beetles.

By comparison, the unloaded "blank control" traps caught no snout beetles. Similar test were also conducted for other substances—51 in total, but no snout beetles were caught in any of them, apart from those mentioned above. There are no attractants registered for use on snout beetles on deciduous fruit in South Africa with which to compare the above results.

Experimental Procedure for Combined Odorants

Equal parts of the compounds Cyclopropane carboxylic acid, 5-Methyl-2-hexanone, 2,5-Dimethyl-4-methoxy-3(2H)-furanone, and Anisole, by volume, were combined and the combination used to fill capsules with polymeric walls that are sufficiently pervious to serve as a reticular diffusion membrane, through which the compounds can escape very slowly by diffusion, over extended periods.

3-Methoxy acetophenone is quite viscous and was diluted in a 20% solution in water.

The solution was applied to surfaces of mechanical traps and the filled capsules were placed in the traps and the traps were placed in the same orchards described above. The snout beetles caught in the traps were too numerous to record accurately, but it was quite clear that the odorant attractants were acting synergistically and were extremely effective in attracting the snout beetles.

The invention claimed is:

1. An odorant substance for use as an attractant for snout beetles, said odorant substance including each of the following compounds: Cyclopropane carboxylic acid, 5-Methyl-2-hexanone, 2,5-Dimethyl-4-methoxy-3(2H)-furanone, and Anisole.

2. An odorant substance as claimed in claim 1, characterised in that said compounds are included in said substance in about equal parts, by volume.

3. An odorant substance as claimed in claim 1, characterised in that said substance is contained in a capsule with a polymeric wall through which said compounds can pass by diffusion.

4. An odorant substance as claimed in claim 1, characterised in that said substance further includes 20% 3-Methoxy acetophenone, diluted in water, by volume.

5. An odorant substance as claimed in claim 1, characterised in that said substance further includes 3-Methoxy acetophenone.

6. A method of controlling snout beetles, characterised by the step of applying an odorant substance to attract the snout beetles, said odorant substance including at least one of the following compounds:
Cyclopropane carboxylic acid;
5- Methyl-2-hexanone;
2,5-Dimethyl-4-methoxy-3(2H)-furanone;
Anisole; and
3-Methoxy acetophenone.

7. A method as claimed in claim 6, characterised by applying said odorant substance in a mechanical trap.

8. A method as claimed in claim 7, characterised by placing a capsule containing at least one of Cyclopropane carboxylic acid, 5-Methyl-2-hexanone, 2,5-Dimethyl-4-methoxy-3(2H)-furanone, and Anisole in said mechanical trap, said capsule having a polymeric wall through which said compounds can pass by diffusion.

9. A method as claimed in claim 8, characterised in that each of said Cyclopropane carboxylic acid, 5-Methyl-2-hexanone, 2,5-Dimethyl-4-methoxy-3(2H)-furanone, and Anisole is contained in said capsule, in generally equal parts, by volume.

10. A method as claimed in claim 7, characterised by applying a 20% dilution of said 3-Methoxy acetophenone in water, by volume, to a surface of said mechanical trap.

11. A method as claimed in claim 6, characterised by combining said odorant substance with an insecticide.

12. A method as claimed in claim 6, characterised in that the snout beetles are Eremnus setulosus.

13. A method as claimed in claim 6, characterised in that the snout beetles are *Phlyctinus calosus*.

* * * * *